United States Patent [19]

Kojima et al.

[11] Patent Number: 4,814,143
[45] Date of Patent: Mar. 21, 1989

[54] EXHAUST-GAS ANALYZING DEVICE

[75] Inventors: Mitoku Kojima, Okazaki; Hiroji Kohsaka, Kusatsu; Hisao Matsui, Yasu, all of Japan

[73] Assignee: Horiba, Ltd., Kyoto, Japan

[21] Appl. No.: 81,370

[22] Filed: Aug. 4, 1987

[30] Foreign Application Priority Data

Aug. 7, 1986 [JP] Japan ................................ 61-184143

[51] Int. Cl.$^4$ ............................................. G01N 7/00
[52] U.S. Cl. ........................................ 422/83; 436/143
[58] Field of Search ................... 422/83, 112; 436/143

[56] References Cited

U.S. PATENT DOCUMENTS

| 4,040,783 | 8/1977 | Collin | 422/83 |
| 4,061,467 | 12/1977 | Becker et al. | 422/83 |
| 4,257,439 | 3/1981 | Mayeaux | 422/112 |
| 4,335,073 | 6/1982 | Sherwood et al. | 422/83 |

Primary Examiner—Benoit Castel
Assistant Examiner—T. J. Wallen
Attorney, Agent, or Firm—Wenderoth, Lind & Ponack

[57] ABSTRACT

In a low-pressure testing apparatus for analyzing gas exhausted from cars under a condition in which air pressure is low, an exhaust-gas analyzing device is provided with a dilution tunnel for diluting exhaust gas from cars with air which is under a decompressed condition, the exhaust-gas analyzer is connected to said dilution tunnel at a supply port side thereof and arranged in a low-pressure testing room, and an exhaust intake is open to the air outside of the low-pressure testing room via airtight piping. An influence caused by the fluctuation of pressure within the low-pressure testing room upon the accuracy of anaylsis can be eliminated.

3 Claims, 3 Drawing Sheets

EXHAUST-GAS ANALYZING DEVICE

BACKGROUND OF THE INVENTION

1. Field of the Invention

The present invention relates to an analyzing device for analyzing gas exhausted from cars.

2. Description of the Prior Art

In order to reduce a distance (l in FIG. 3) from a sample-inlet of a dilution tunnel 6 for diluting exhaust gas from cars with air which is in a decompressed condition, that is to say air within a low-pressure testing room, to an exhaust-gas analyzer 8, the exhaust-gas analyzer has been arranged in the low-pressure testing room. That is to say, a construction as shown in FIG. 3 has been used. Referring to FIG. 3, reference numeral 1 designates a low-pressure testing room, reference numeral 2 designates atmosphere pressure, reference numeral 3 designates a decompression blower, reference numeral 4 designates a car, reference numeral 5 designates a chassis dynamometer, reference numeral 6 designates a dilution tunnel, reference numeral 7 designates air, reference numeral 8 designates an analyzer, reference numeral 9 designates an overflow line, reference numeral 10 designates a zero gas passage, reference numeral 11 designates a span gas passage, reference numeral 12 designates a bag sample passage, and reference numeral 13 designates a valve.

When HC (hydrocarbon) is measured, if the temperature is reduced, certain kinds of HC do not assume a gaseous state, so that it is necessary to maintain the temperature high and therefore, l has been reduced. For example, such is the case when an HC analyzer is used as an exhaust-gas analyzer.

An exhaust-gas analyzer for use with a car is influenced with respect to its analytical sensitivity by a fluctuation in atmospheric pressure. Although the accuracy of the exhaust-gas analysis is not influenced by the fluctuation of atmospheric pressure in nature at the same altitude, if atmospheric pressure is reduced to about a half atm. as occurs in the low-pressure testing room, for example, the pressure of air is reduced to 460 to 400 mmHg, as a result, the accuracy of the exhaust-gas analysis is diminished. The conventional analyzer has not taken measures for solving the above-described problem. Therefore, according to the known method, the measurement is carried out under a condition in which the accuracy is reduced in dependence upon a degree of the setting of pressure in the low-pressure testing room, or, in which pressure is calibrated (this is not easy) and then data is read.

SUMMARY OF THE INVENTION

It is an object of the present invention to provide an exhaust-gas analyzing device capable of reducing an influence caused by the fluctuation of atmospheric pressure within a low-pressure testing room upon the accuracy of the analyzer in view of the above-described problems of the prior art. An exhaust-gas analyzing device in a low-pressure testing apparatus for analyzing gas exhausted from cars under a condition in which the pressure of air is low, according to the present invention, is characterized in the provision of a dilution tunnel for diluting exhaust gas from cars with air which is in a decompressed condition, an exhaust-gas analyzer connected with said dilution tunnel at a supply port side thereof and arranged in said low-pressure testing room, and an exhaust intake open to the air outside of the low-pressure testing room via airtight piping.

Accordingly, since the accuracy of the analyzer is the same as when the analyzer is arranged under an atmospheric condition in which the sample-exhausting system of the analyzer is arranged in the outside air, an influence caused by the fluctuation of atmospheric pressure within the low-pressure testing room upon the accuracy of the analyzer is reduced by placing the exhaust pipe in open communication with the air in an airtight manner and by providing a pressure pump in the sample-supply system.

DETAILED DESCRIPTION OF THE PREFERRED EMBODIMENTS

The preferred embodiments according to the present invention will be described below with reference to the drawings.

Figure 1:
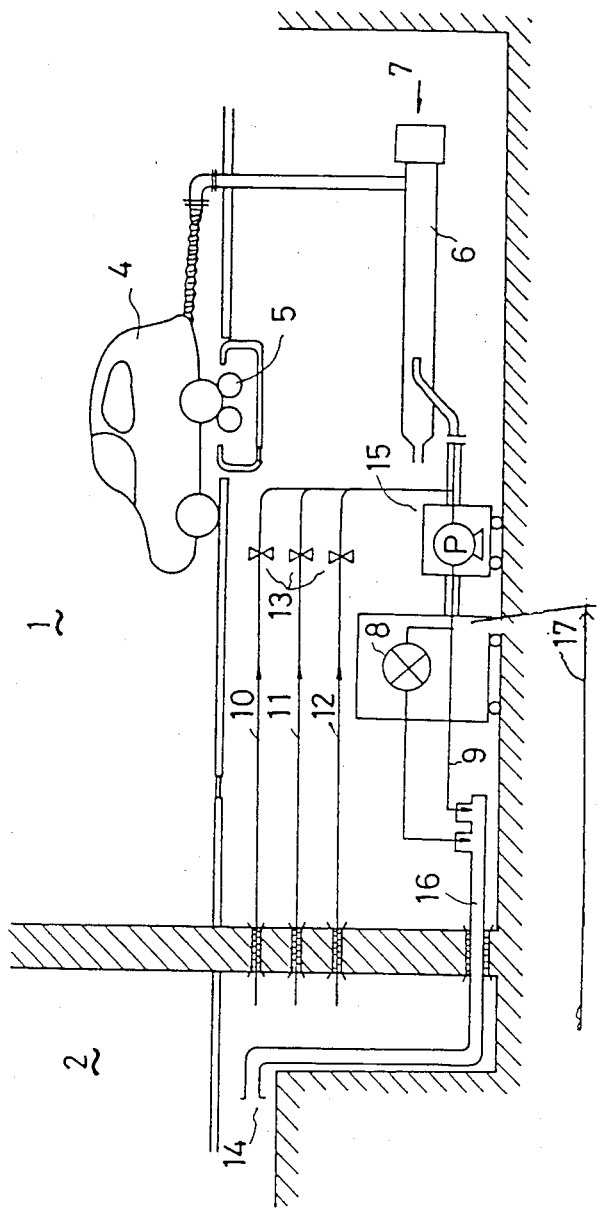
FIG. 1 is a diagram showing an apparatus according to one preferred embodiment of the present invention.

FIG. 1 is a diagram showing an apparatus according to one preferred embodiment of the present invention.

Figure 3:
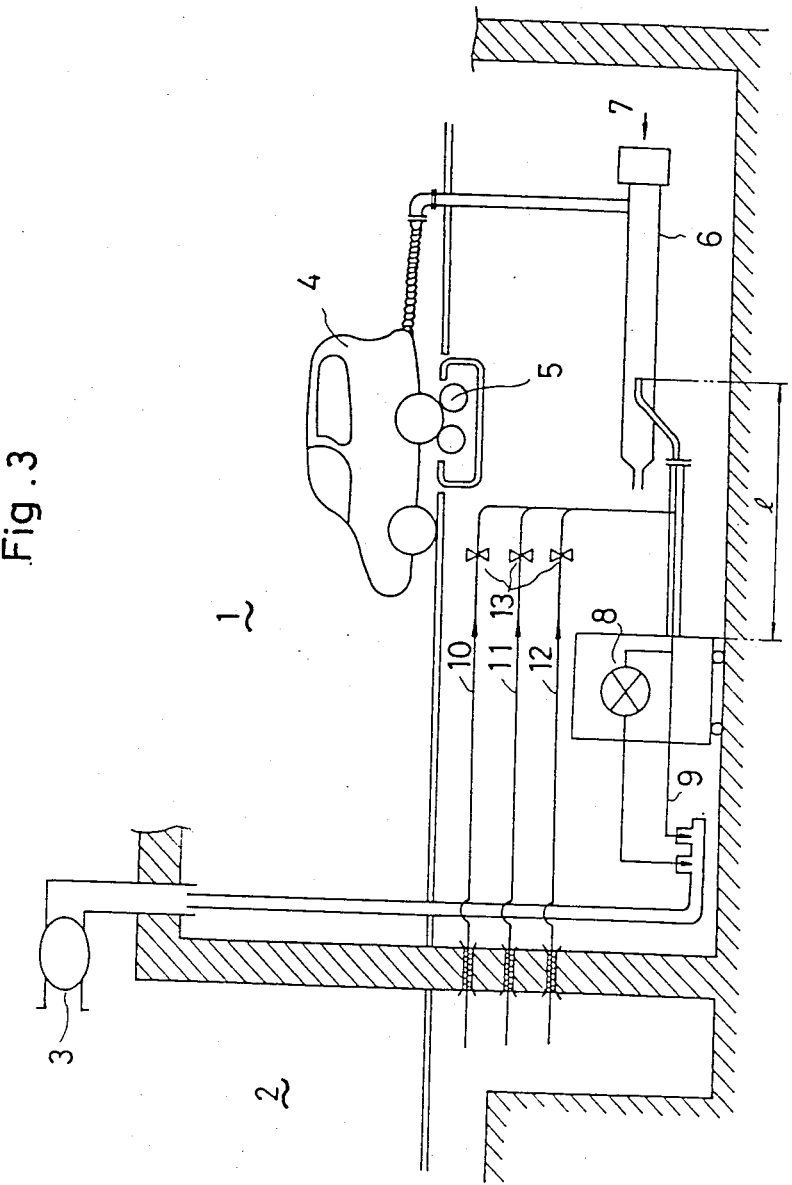
FIG. 3 is a diagram showing a conventional apparatus.

Referring to FIG. 1, reference numerals 1, 2, 4 to 13 designate the same members as in FIG. 3 showing the conventional apparatus.

Reference numeral 14 designates an opening at an air side of an exhaust-pipe 16 connected to the analyzer and reference numeral 15 designates a pressure pump provided in the sample-supply system. In addition, reference numeral 17 designates nearly 1 atm.

The operation of the above-described apparatus is described below.

According to the present invention, since the sensitivity of the analyzer 8 is under the same condition as if the analyzer 8 was disposed under an atmospheric pressure, an influence caused by the fluctuation of pressure within the low-pressure testing room upon the accuracy of the analyzer 8 is reduced by placing the exhaust pipe in open communication with outside air in an airtight manner and by providing the pressure pump 15 in the sample-supply system.

Figure 2:
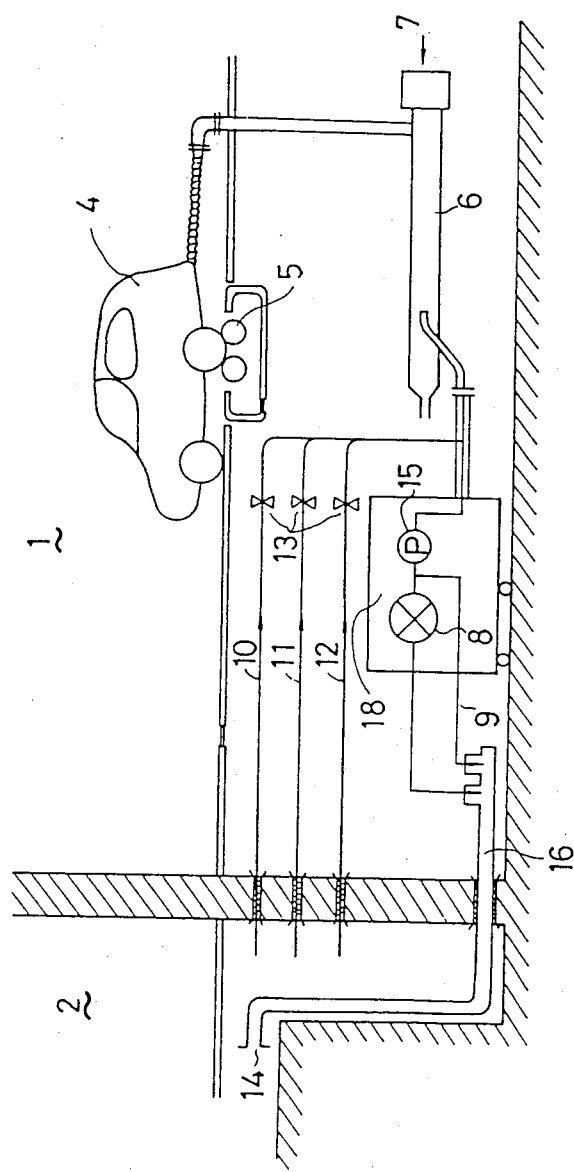
FIG. 2 is a diagram showing an apparatus according to another preferred embodiment of the present invention.

FIG. 2 is a diagram showing an apparatus according to another preferred embodiment of the present invention.

The apparatus of FIG. 2 is different from the apparatus of FIG. 1 merely in that the pressure pump 15 is included in an analyzing portion 18. The operation and effects are the same.

The present invention exhibits the following effect.

An influence caused by the fluctuation of pressure within the low-pressure testing room upon the accuracy of analysis can be eliminated.

What is claimed is:

1. An exhaust gas analyzing device for analyzing exhaust gas from a vehicle, said device comprising:
    a low pressure testing room in which air is maintained under pressure lower than atmospheric pressure;
    a tunnel through which exhaust gas of a vehicle is fed, said tunnel disposed in said low pressure testing room and open thereto for diluting the exhaust gas fed therethrough with the air in the low pressure room;

a pressure pump disposed in said low pressure testing room and in communication with said tunnel for pumping a sample of exhaust gas dilluted in said tunnel under a predetermined pressure, said pressure pump having a supply port open to said tunnel for establishing the communication of the pump therewith and through which the sample passes from the tunnel to the pump; and an exhaust gas analyzer means disposed in said low pressure testing room for analyzing the exhaust gas, said exhaust gas analyzer means having an intake and an exhaust pipe, said intake operatively connected to said pressure pump for introducing exhaust gas pumped under said predetermined pressure by said pump to the exhaust gas analyzer means, and said exhaust pipe extending in said low pressure testing room in an air-tight manner and open to the atmosphere outside of said low pressure testing room.

2. An exhaust gas analyzing device as claimed in claim 1, and further comprising an enclosure disposed in said low pressure testing room and in which the exhaust gas is analyzed, said exhaust gas analyzer means and said pressure pump enclosed in said enclosure.

3. An exhaust gas analyzing device as claimed in claim 1, wherein said low pressure testing room is one in which air is maintained under a low pressure of approximately one half of an atmosphere.

* * * * *